United States Patent
Elgas et al.

[11] Patent Number: 5,935,093
[45] Date of Patent: Aug. 10, 1999

[54] SOFTSHELL RESERVOIR WITH INTEGRATED CARDIOTOMY RESERVOIR

[75] Inventors: Roger J. Elgas, Anaheim; Robert G. Gremel, Huntington Beach; Michael R. Van Driel, Fountain Valley, all of Calif.

[73] Assignee: Medtronic, Inc., Minneapolis, Minn.

[21] Appl. No.: 08/940,072

[22] Filed: Sep. 29, 1997

[51] Int. Cl.⁶ .................................................. A61M 37/00
[52] U.S. Cl. .................. 604/4; 422/44; 422/45; 604/5; 604/8; 210/472
[58] Field of Search ................ 210/472; 604/4, 604/5, 8; 422/45, 44

[56] References Cited

U.S. PATENT DOCUMENTS

| | | | |
|---|---|---|---|
| 3,827,860 | 8/1974 | Burlis | 23/258.5 |
| 3,892,534 | 7/1975 | Leonard | 23/258.5 |
| 3,918,912 | 11/1975 | Talonn | 23/258.5 |
| 4,602,910 | 7/1986 | Larkin | 604/87 |
| 4,717,377 | 1/1988 | Fukasawa | 604/4 |
| 4,734,269 | 3/1988 | Clarke et al. | 422/310 |
| 4,737,139 | 4/1988 | Zupkas et al. | 604/4 |
| 4,795,457 | 1/1989 | Cooney | 604/408 |
| 4,863,452 | 9/1989 | Irmiter et al. . | |
| 4,959,062 | 9/1990 | Gellman | 604/403 |
| 5,049,146 | 9/1991 | Bingham et al. | 604/4 |
| 5,061,236 | 10/1991 | Sutherland et al. | 604/4 |
| 5,158,533 | 10/1992 | Strauss et al. | 604/4 |
| 5,322,625 | 6/1994 | Rise | 210/238 |
| 5,411,705 | 5/1995 | Thor et al. | 422/45 |
| 5,573,526 | 11/1996 | Hess . | |
| 5,770,073 | 6/1998 | Bach et al. | 210/472 |

FOREIGN PATENT DOCUMENTS 0 401 016  5/1990  European Pat. Off. .
WO 97 33672  9/1997  WIPO .

OTHER PUBLICATIONS

Schonberger, J P; Systemic blood activation with open and closed venous reservoirs. Annals of Thoracic Surgery 59 pp. 1549–1555, Jun. 1995.

Ochsner, J L; A venous reservoir for cardiopulmonary bypass in newborns and infants. Annals of Thoracic Surgery, 45, p. 686, Jun. 1988.

*Primary Examiner*—John G. Weiss
*Assistant Examiner*—Cheryl L. Huseman
*Attorney, Agent, or Firm*—Harry G. Weissenberger

[57] ABSTRACT

A softshell blood reservoir incorporates an integral flexible cardiotomy section in which a filter/defoamer unit is supported in a semirigid cage. The reservoir also incorporates a storage section and a mixing section. The three sections can selectively communicate with each other. Cardiotomy blood is supplied to the cardiotomy section, and venous blood is supplied to the mixing section. The storage section holds varying amounts of cardiotomy blood to maintain a constant mixed blood output from the mixing section. Only the filter/defoamer unit and the mixing section need be primed.

6 Claims, 2 Drawing Sheets

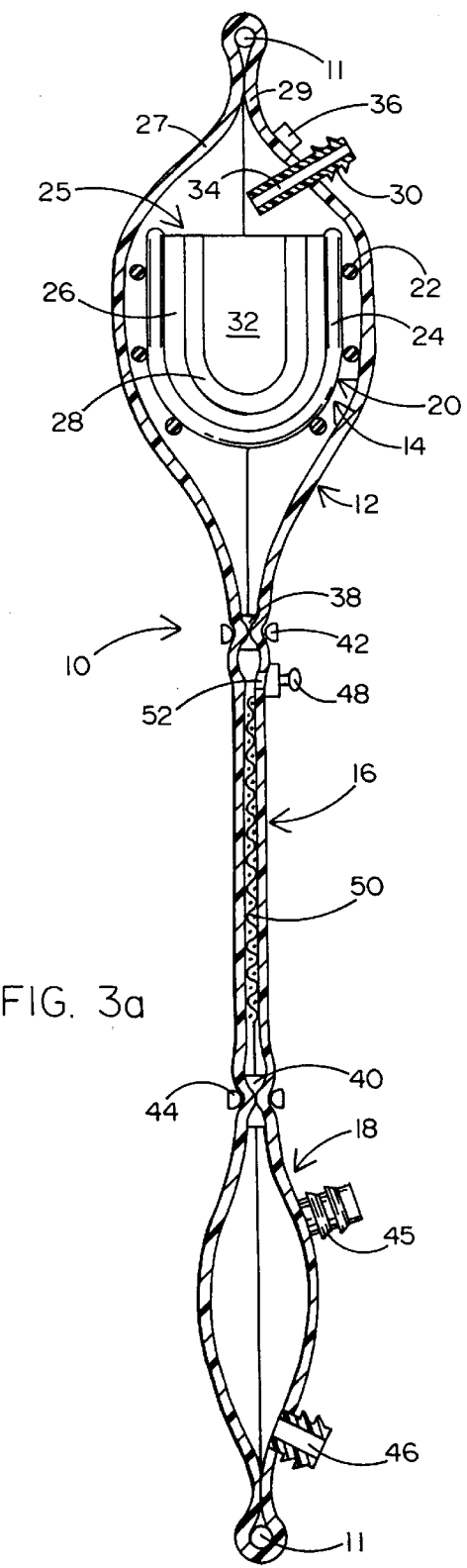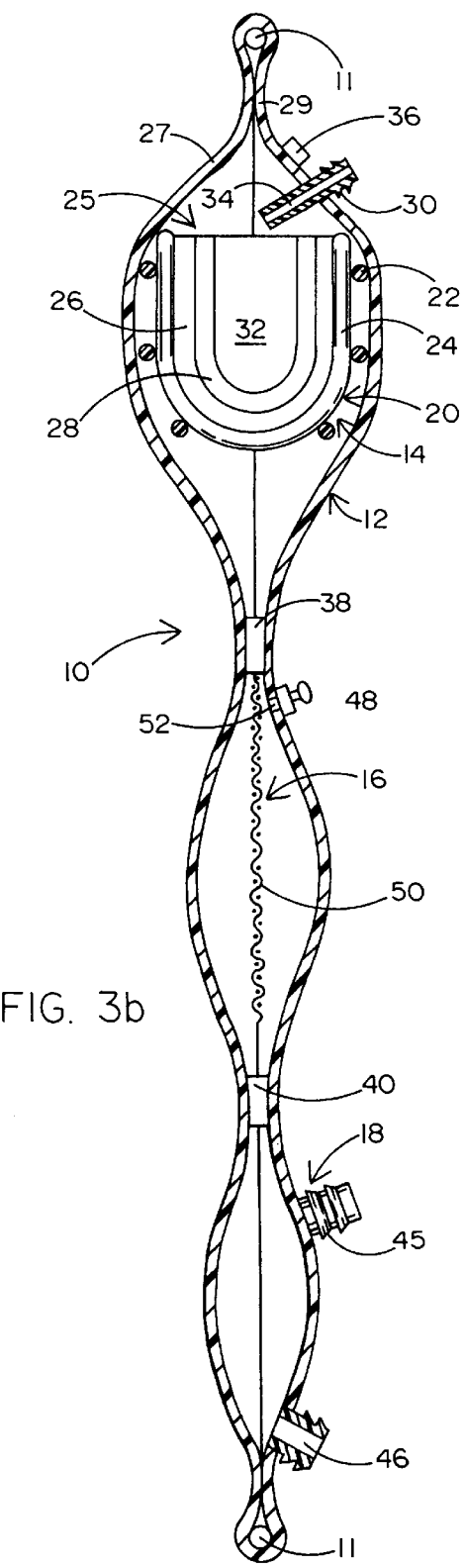

5,935,093

SOFTSHELL RESERVOIR WITH INTEGRATED CARDIOTOMY RESERVOIR

FIELD OF THE INVENTION

This invention relates to softshell blood reservoirs used in cardiac surgery, and more particularly to a combination softshell and cardiotomy reservoir featuring a low priming volume.

BACKGROUND OF THE INVENTION

A typical extracorporeal surgical blood circuit such as the blood circuit associated with a heart-lung machine in cardiovascular bypass surgery contains, among other elements, a cardiotomy reservoir and a softshell reservoir. The cardiotomy reservoir receives blood and debris sucked from the surgery field, and filters and defoams it for oxygenation in the heart-lung machine and eventual return to the patient's circulatory system. The filtered and defoamed cardiotomy blood is mixed in the softshell reservoir with venous blood from the patient's vena cava, and the mixed blood is then conveyed to the blood pump of the heart-lung machine.

Because the total blood supply to the softshell reservoir is sometimes more and sometimes less than the blood demand of the heart-lung machine's blood pump, the softshell reservoir must store enough blood to absorb any blood input fluctuations while supplying a steady blood flow to the pump.

A major problem in cardiovascular bypass surgery is the priming of the blood circuit. Before pumping blood through the heart-lung machine's oxygenator and back into the patient's circulatory system, all air must be purged from the blood circuit. This is done by priming, i.e. filling the blood circuit with saline solution. When the patient is connected to the heart-lung machine, the saline solution in the circuit is discharged into the patient's circulatory system and eventually mixes with the patient's blood. Because this at least temporarily makes the blood in the patient's circulatory system nonhomologous, and even after thorough mixing leaves the patient anemic for several days, it is important to minimize the priming volume of the blood circuit in every possible way.

One of the components that contributes significantly to the priming volume is the tubing that interconnects the various operational elements of the blood circuit. For that reason, and also for convenience of set-up and disposal as well as for economic considerations, it is desirable to consolidate as many blood circuit elements as possible into a single element that requires no interconnecting tubing and has a low priming volume.

Another problem in the blood circuit is that cardiotomy blood that remains too long in proximity to the cardiotomy filter-defoamer elements tends to start clotting and causing difficulties in the circuit.

SUMMARY OF THE INVENTION

The invention overcomes the above-identified problems of the prior art by consolidating, in a single softshell bag, a low-prime cardiotomy reservoir with a filter-defoamer, a blood storage reservoir that does not need to be primed, and a low-prime mixing chamber for mixing the cardiotomy blood with venous blood drawn directly from the patient's circulatory system. In the inventive combination reservoir, these three components are interconnected by short passages that can be clamped closed for priming and opened for blood circulation.

BRIEF DESCRIPTION OF THE DRAWINGS

FIG. 3a is a vertical section along line 3—3 of FIG. 1 during priming; and

FIG. 3b is a vertical section along line 3—3 of FIG. 1 during use.

DESCRIPTION OF THE PREFERRED EMBODIMENT

Figures 1, 2:
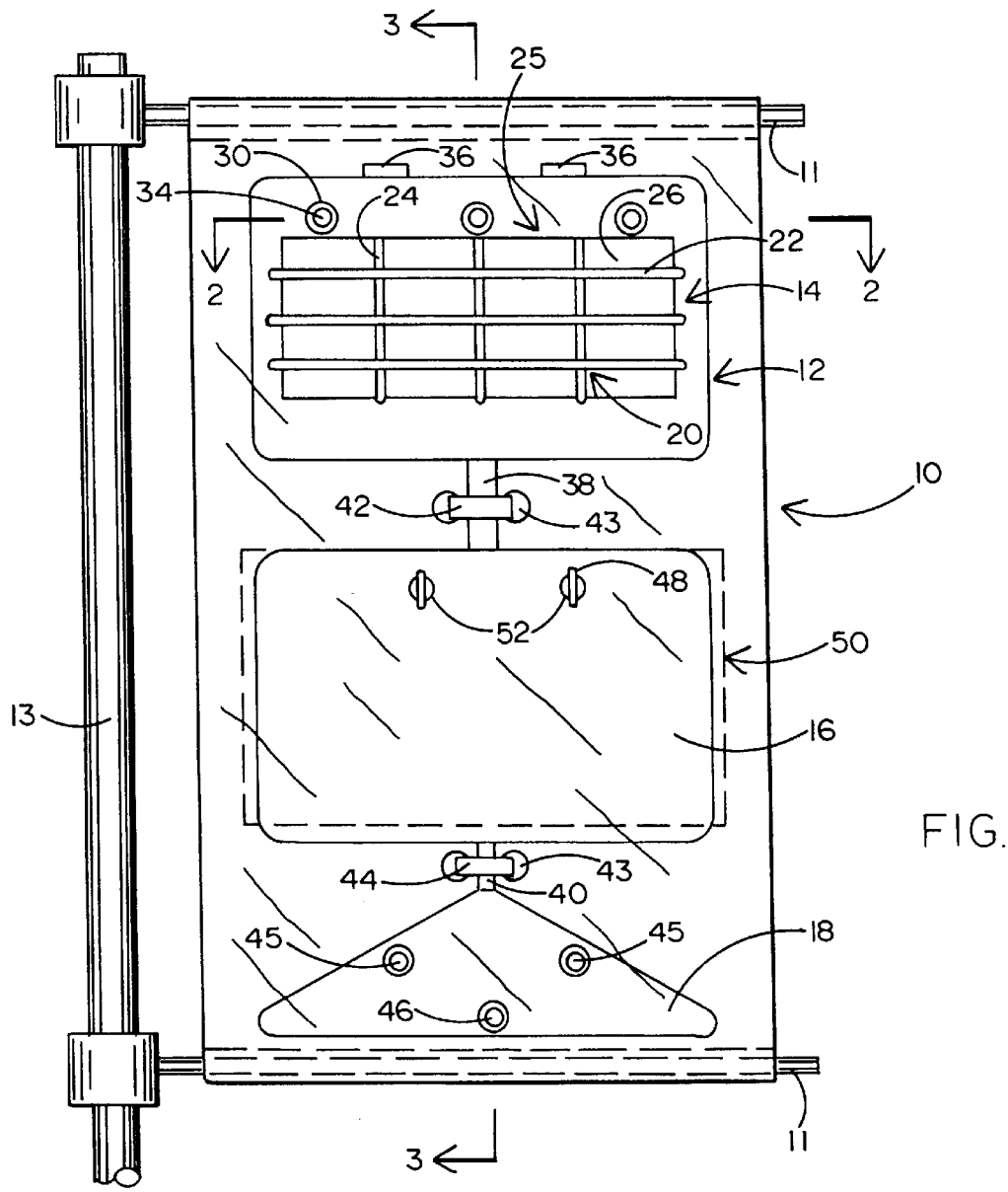
FIG. 1 is a front elevation of the combination reservoir of this invention.
FIG. 2 is a horizontal section along line 2—2 of FIG. 1.

As best shown in FIG. 1, the combination reservoir 10, which in use is preferably suspended from arms 11 mounted on a support pole 13, consists of three vertically stacked and separately expandable interconnected components: a cardiotomy section 12 with a filter-defoamer pack 14; a softshell storage section 16; and a softshell mixing section 18.

The cardiotomy section 12 is basically a vented softshell reservoir, but unlike ordinary softshell reservoirs, which are flat and have zero volume prior to priming, the section 12 is always expanded in order to accommodate therein the filter-defoamer pack 14. The pack 14 includes a semirigid cage 20 of oval horizontal plastic rods 22 and U-shaped vertical plastic rods 24. The cage 20 supports therein a conventional filter/defoamer unit 25 consisting essentially of an outer filter layer 26 and an inner defoamer layer 28. A second defoamer layer (not shown) on the outside of the filter layer 26 may also advantageously be used in accordance with conventional filtering/defoaming practice. The filter/defoamer unit 25 is open at its top and closed at its bottom. Cardiotomy inlet ports 30 on the outside of the reservoir 10 communicate with the interior 32 of the filter/defoamer unit 25 through conduits 34 to introduce raw cardiotomy blood into the filter/defoamer unit 25.

As will best be seen in FIG. 2, the horizontal rods 22 and the vertical rods 24 of the cage 20 are radially outwardly displaced from one another. This prevents the flexible walls 27, 29 of the cardiotomy section 12, which tend to squeeze the semirigid cage 20, from coming close enough to the filter layer 26 to impede the outflow of blood therefrom.

Because the cardiotomy section 12 is vented to atmosphere by vents 36 and is therefore not a closed vessel, priming of the section 12 need only be done enough to wet the filter/defoamer unit 25. With a cardiotomy section 12 of about 1,000 ml total capacity, about 100 cc of priming saline is sufficient to wet the unit 25.

Priming is done, as shown in FIG. 3a, with the passages 38 and 40 between the sections 12, 16 and 18 of the combination reservoir 10 closed off by conventional clamps 42 and 44, respectively, which pass through apertures 43 in the reservoir 10. Thus the priming saline used in wetting the filter/defoamer unit 25 temporarily stays in the cardiotomy section 12. At the same time, the small mixing reservoir can be primed with as little as 50 ml of saline solution introduced through the venous inlet ports 46.

When the patient is connected to the heart-lung machine (not shown), the clamps 42, 44 are released as shown in FIG. 3b, and filtered cardiotomy blood begins to fill the storage section 16 and run from there into the mixing section 18 where it mixes with the venous blood introduced into the mixing section 18 through one or more of the inlets 45. It is important that filtered cardiotomy blood be removed from the cardiotomy section 12 as soon as possible, as cardiotomy blood that remains in close proximity to the filter/defoamer pack 14 after filtering has a tendency to clot. Two inlets 45 are preferably provided to allow venous blood to be conveniently brought in from either the right or the left of the reservoir 10, as described and claimed in copending application Ser. No. 08/939,382 filed on even date herewith and entitled "Bilaterally Connectable Softshell Reservoir". Unused ones of the inlets 36 and 45 are plugged by appropriate plugs (not shown).

Theoretically, the total inflow of venous blood plus cardiotomy blood into the combination reservoir 10 should exactly match the outflow of mixed blood from the mixing section 18 through outlet port 46 to the heart-lung machine. In practice, however, this is not always true. Although the pump of the heart-lung machine draws a fairly constant stream of blood from the outlet port 46, the inflow rate of blood from the patient, particularly in the cardiotomy circuit, fluctuates from time to time. Consequently, the roughly 800 ml storage section 16 acts as a buffer that discharges cardiotomy blood into mixing section 18 at a varying rate, and may even momentarily receive blood from mixing section 18 if a venous input surge occurs.

The details and advantages of the preferred embodiments of the storage section 16 and mixing section 18, as well as of the microair trap screen 50 which is shown herein an optional form as being provided only in the storage section 16, are described in copending application Ser. No. 08/939, 383filed on even date herewith and entitled "Two-chambered Softshell Reservoir". Suffice it to say that microair bubbles trapped by the screen 50 may be vented through purge ports 52 that may be opened or closed by conventional stopcocks 48. Microair in section 16 cannot be vented through vents 36 because of the constant downward flow of cardiotomy blood through passage 38.

It will be seen that the combination reservoir 10 of this invention not only allows a low priming volume, but also, by doing away with a separate cardiotomy reservoir, reduces cost and space requirements in the operating room, and facilitates the set-up and disposal of the extracorporeal blood circuit components in cardiac surgery.

It is understood that the exemplary softshell reservoir with integrated cardiotomy reservoir described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

We claim:

1. A softshell blood reservoir, comprising:

a) a cardiotomy section, a storage section, and a mixing section, said sections being individually expandable and selectably interconnectable;

b) a filter/defoamer unit disposed in said cardiotomy section, said cardiotomy section being arranged to receive cardiotomy blood, to discharge it into said filter/defoamer unit, and to collect filtered cardiotomy blood put out by said unit;

c) said storage section being arranged to receive filtered cardiotomy blood from said cardiotomy section when interconnected therewith, and to discharge it into said mixing section when interconnected therewith; and d) said mixing section being arranged to receive venous blood from the exterior of said reservoir and filtered cardiotomy blood from said storage section, and to discharge a mixture of both to the exterior of said reservoir.

2. The reservoir of claim 1, further comprising:

e) a cage structure disposed in said cardiotomy section, said cage structure being arranged to support said filter/defoamer unit, and to maintain the outside of said filter/defoamer unit spaced from the walls of said cardiotomy section.

3. The reservoir of claim 2, in which said cage structure is composed of intersecting substantially vertically and substantially horizontally extending rods, said horizontally and vertically extending rods being differently spaced from said filter/defoamer unit.

4. The reservoir of claim 1, further comprising:

e) a microair bubble trap screen extending through said storage and mixing sections, said storage section having at least one selectably openable air purge port formed in the top thereof.

5. The reservoir of claim 1, in which said sections are vertically disposed above one another, with said cardiotomy section on top, said storage section in the middle, and said mixing section on the bottom.

6. The reservoir of claim 2, in which said cage is semirigid, and said filter/defoamer unit is substantially oval in horizontal cross section.

* * * * *